United States Patent
Ohno

(10) Patent No.: US 8,831,325 B2
(45) Date of Patent: Sep. 9, 2014

(54) RADIOGRAPHIC IMAGE PROCESSING APPARATUS AND RADIOGRAPHIC IMAGE PROCESSING PROGRAM

(75) Inventor: Yoshinori Ohno, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 208 days.

(21) Appl. No.: 13/519,773

(22) PCT Filed: Dec. 29, 2009

(86) PCT No.: PCT/JP2009/007368
§ 371 (c)(1),
(2), (4) Date: Jun. 28, 2012

(87) PCT Pub. No.: WO2011/080808
PCT Pub. Date: Jul. 7, 2011

(65) Prior Publication Data
US 2012/0288179 A1  Nov. 15, 2012

(51) Int. Cl.
*G06K 9/00* (2006.01)
*G06K 9/34* (2006.01)
*G06K 9/40* (2006.01)
*A61B 6/00* (2006.01)
*G06T 7/00* (2006.01)

(52) U.S. Cl.
CPC ............ *G06T 7/0083* (2013.01); *A61B 6/4233* (2013.01); *G06T 2207/30004* (2013.01); *A61B 6/5258* (2013.01); *G06T 2207/10116* (2013.01); *G06T 2207/20056* (2013.01); *G06T 7/0095* (2013.01); *G06T 2207/20064* (2013.01); *G06T 2207/20061* (2013.01)
USPC ............ 382/132; 382/173; 382/263; 382/264

(58) Field of Classification Search
CPC ..................... G06T 2207/10116; G06T 7/079; G06T 3/40; G06K 9/00503
USPC .................................. 382/132, 173, 263, 264
See application file for complete search history.

(56) References Cited

U.S. PATENT DOCUMENTS 6,243,485 B1 *  6/2001  Murakami ..................... 382/132
6,885,770 B2 *  4/2005  Matsuura ...................... 382/199

(Continued)

FOREIGN PATENT DOCUMENTS

JP   2001-331800 A   11/2001
JP   2006-181362      7/2006

(Continued)

OTHER PUBLICATIONS

Chinese Office Action issued in Application No. 200980163236.4 dated May 6, 2014.

*Primary Examiner* — Utpal Shah
(74) *Attorney, Agent, or Firm* — McDermott Will & Emery LLP

(57) ABSTRACT

A radiographic image processing apparatus in this invention decreases a spatial resolution twice in total by a low-frequency image generating device and a low-frequency characteristic generating device. Thereby an influence such as noise and thus calculation amounts are decreased. Moreover, excessive characteristic amounts (patterns) not removed among characteristic amounts extracted through the low-frequency image generating device and a characteristic extracting device can be decreased by decrease of the spatial resolution by the low-frequency characteristic generating device. Consequently, influence such as noise and calculation amounts can be decreased for the low-frequency characteristics generated by the low-frequency characteristic generating device and a radiation area extracted by an area extracting device on the latter stage. As a result, influences such as noise can be decreased for achieving characteristic extraction and area extraction with high accuracy, and thus calculation amounts can be decreased.

11 Claims, 4 Drawing Sheets

(56) References Cited

U.S. PATENT DOCUMENTS

| | | | |
|---|---|---|---|
| 7,508,970 B2 * | 3/2009 | Jabri et al. | 382/132 |
| 7,636,476 B2 * | 12/2009 | Takahashi | 382/199 |
| 7,636,495 B2 * | 12/2009 | Shinbata | 382/274 |
| 7,724,934 B2 * | 5/2010 | Shinbata | 382/132 |
| 7,801,344 B2 * | 9/2010 | Wang | 382/128 |
| 2002/0031246 A1 | 3/2002 | Kawano | |
| 2002/0114504 A1 * | 8/2002 | Shinbata | 382/132 |
| 2002/0154800 A1 * | 10/2002 | Shinbata | 382/132 |
| 2006/0140483 A1 | 6/2006 | Jabri et al. | |
| 2006/0269141 A1 | 11/2006 | Takahashi | |
| 2010/0215243 A1 | 8/2010 | Ohno | |

FOREIGN PATENT DOCUMENTS

| | | |
|---|---|---|
| JP | 2007-041664 | 2/2007 |
| JP | 4280729 | 6/2009 |
| WO | WO 2009/044452 A1 | 4/2009 |

* cited by examiner

3

RADIOGRAPHIC IMAGE PROCESSING APPARATUS AND RADIOGRAPHIC IMAGE PROCESSING PROGRAM

CROSS REFERENCE TO RELATED APPLICATIONS

This application is a U.S. National Stage application under 35 U.S.C. §371, of International Application PCT/JP2009/007368 filed on Dec. 29, 2009, which was published as WO 2011/080808 on Jul. 7, 2011. The application is incorporated herein by reference.

TECHNICAL FIELD

This invention relates to a radiographic image processing apparatus and a radiographic image processing program for processing a radiographic image having undergone radiography.

BACKGROUND ART

In a radiographic image processing apparatus, image processing is performed through intercepting a portion of direct radiation (direct rays) by a lead sheeting, etc., that intercepts radiation for suppressing decrease in contrast of a radiographic image due to influence of scattered radiation (scattered rays) or for avoiding unnecessary exposure to extract a radiation area. In this case, the radiographic image having undergone radiography needs to be optimized to have a suitable gradation. A radiation area needs to be extracted from the radiographic image for controlling a dose of radiation transmitting through a subject upon radiography.

Thus there exists a technique that a plurality of combinations of two candidate points is generated from an image acquired from a radiation detector, an evaluated value is obtained to each candidate, and the candidate with a higher value is extracted as a contour of a radiation area. See, for example, Patent Literature 1. There also exists a technique that characteristic amounts are extracted from a blurred image having a lower frequency than a radiographic image, and a contour of the radiation area by a collimator (also referred to as a "collimator edge" or "collimation edge") is extracted. See, for example, Patent Literature 2. Here in the field of image processing, a process for extracting components for discrimination is called "characteristic extraction" in description of an image.

[Patent Literature 1] Japanese Patent No. 4280729
[Patent Literature 2] Japanese Patent Publication No. 2006-181362A In Patent Literature 1 as a conventional technique, characteristic points are extracted from the entire image data by filtering, derivation, etc. Consequently, when noise is contained in the image, not only the necessary characteristic corresponding to an edge of the radiation area but also other many unnecessary characteristic points are to be detected. As a result, a problem of decreasing detection accuracy may arise.

The extracted edge points are classified into groups for selecting a characteristic. When many characteristic points are detected, combination of candidate points may increase in number, which leads to complicated calculation. Moreover, a collimator is mostly rectangular. As a result, the radiation area has a rectangular shape, and accordingly the edge of the radiation area is of straight line pattern. On the other hand, a problem also arises that even excessive patterns (e.g., straight line data on sides of a subject) may be detected.

This invention has been made having regard to the state of the art noted above, and its object is to provide a radiographic image processing apparatus and a radiographic image processing program that enables characteristic extraction and area extraction with high accuracy under reduced influences, such as noise, and decreased amounts of calculation.

SUMMARY

This invention is constituted as stated below to achieve the above object. A radiographic image processing apparatus of an example of this invention is a radiographic image processing apparatus for processing a radiographic image having undergone radiography. The apparatus includes a low-frequency image generating device for generating a low-frequency image having a lower frequency than the radiographic image through decreasing a spatial resolution of the radiographic image; a characteristic extracting device for performing characteristic extraction through determining characteristic amounts in accordance with signal level differences between any pixel of the low-frequency image and peripheral pixels thereof and generating a characteristic image by bringing the characteristic amounts into correspondence with each pixel of the low-frequency image; a low-frequency characteristic generating device for generating a low-frequency characteristic as an image having a lower frequency than the radiographic image through decreasing a spatial resolution of the characteristic image; and an area extracting device for selecting a characteristic as an edge of a radiation area based on the low-frequency characteristic, and extracting the radiation area from the radiographic image.

According to the radiographic image processing apparatus in this example of the invention, the low-frequency image generation device generates a low-frequency image having a lower frequency than a radiographic image through decreasing a spatial resolution of the radiographic image. The characteristic extracting device performs characteristic extraction through determining characteristic amounts in accordance with signal level differences between any pixel of the low-frequency image and peripheral pixels thereof and generating a characteristic image by bringing the characteristic amounts into correspondence with each pixel of the low-frequency image. The low-frequency characteristic generating device generates a low-frequency characteristic as an image having a lower frequency than the radiographic image through decreasing a spatial resolution of the characteristic image. The area extracting device selects a characteristic as an edge of a radiation area based on the low-frequency characteristic, and extracts the radiation area from the radiographic image. As noted above, a spatial resolution is decreased twice in total by the low-frequency image generating device and the low-frequency characteristic generating device. Thereby an influence such as noise is reduced and thus calculation amounts are reduced. Moreover, excessive characteristic amounts (patterns) not removed among the characteristic amounts extracted through the low-frequency image generating device and the characteristic extracting device can be decreased by reduction in spatial resolution by the low-frequency characteristic generating device. Consequently, reduction in influence such as noise and in calculation amount can be achieved for the low-frequency characteristics generated by the low-frequency characteristic generating device and the radiation area extracted by the area extracting device on the latter stage. As a result, influences such as noise can be reduced for achieving characteristic extraction and area extraction with high accuracy, and thus calculation amounts can be reduced.

One example of the low-frequency image generating device is a device of generating the foregoing low-frequency image through reducing the radiographic image. Another example of the low-frequency image generating device is a device of generating the foregoing low-frequency image through converting the radiographic image into a spatial frequency area, and then converting a low frequency area of the converted spatial frequency area into a real space. In the former, a spatial resolution of the radiographic image is decreased through reduction of the radiographic image to generate a low-frequency image. In the latter, a spatial resolution of the radiographic image is decreased through converting a low-frequency area of the converted spatial frequency area into a real space to generate a low-frequency image. The low-frequency image may be generated through smoothing by filtering to the radiographic image.

One example of the low-frequency characteristic generating device is a device of generating the foregoing low-frequency characteristic through reduction of the characteristic image. Another example of the low-frequency characteristic generating device is a device of generating the foregoing low-frequency characteristic through converting the characteristic image into a spatial frequency area, and then converting a low-frequency area of the converted spatial frequency area into a real space. In the former, a spatial resolution of the characteristic image is decreased through reduction of the characteristic image to generate a low-frequency characteristic. In the latter, a spatial resolution of the characteristic image is decreased through converting a low-frequency area of the converted spatial frequency area into a real space to generate a low-frequency characteristic. The low-frequency characteristic may also be generated through smoothing by filtering to the characteristic image.

One example of the characteristic extracting device is a device of extracting the characteristic as above through determining a gradient intensity based on signal level differences between the pixel and the peripheral pixels.

Moreover, in the radiographic image processing apparatus in this example of the invention, the area extracting device preferably prepares binary data indicating the presence of a characteristic through binarization of the low-frequency characteristic from a threshold set in advance, and selects a characteristic as an edge of the radiation area based on the binary data. Preparation of the binary data as above can achieve further removal of excessive patterns.

Moreover, in the radiographic image processing apparatus in this example of the invention, using a Hough transform that converts coordinates into a space consisting of a distance of a normal line from the origin point as a reference on a two-dimensional plane to a straight line and an angle constituted by the normal line and an axis as a reference, the coordinates being on the two-dimensional plane, the area extracting device preferably projects the foregoing low-frequency characteristics on the space consisting of the distance and the angle to determine a plurality of sine curves, and detects a straight line as a candidate of an edge of the radiation area based on a point where sine curves intersect each other and a number thereof. The straight line is detected using such a Hough transform, whereby a straight line as a candidate of an edge of the radiation area can be detected with ease.

Moreover, a radiographic image processing program of an example of this invention is a radiographic image processing program for processing a radiographic image by a computer. The program includes a low-frequency image generating step generating a low-frequency image having a lower frequency than the radiographic image through decreasing a spatial resolution of the radiographic image; a characteristic extracting step performing characteristic extraction through determining characteristic amounts in accordance with signal level differences between any pixel of the low-frequency image and peripheral pixels thereof and generating a characteristic image by bringing the characteristic amounts into correspondence with each pixel of the low-frequency image; a low-frequency characteristic generating step generating a low-frequency characteristic as an image having a lower frequency than the radiographic image through decreasing a spatial resolution of the characteristic image; and an area extracting step selecting a characteristic as an edge of a radiation area based on the low-frequency characteristic, and extracting the radiation area from the radiographic image, wherein the computer executes processes in the steps.

According to the radiographic image processing program in this example of the invention, a spatial resolution is decreased twice in total by the low-frequency image generating step and the low frequency characteristic generating step. Thereby an influence such as noise is decreased and thus calculation amounts are decreased. Moreover, excessive characteristic amounts (patterns) not removed among the characteristic amounts extracted through the low-frequency image generating step and the characteristic extracting step can be decreased by reduction in spatial resolution in the low-frequency characteristic generating step. Consequently, reduction in influence such as noise and in calculation amount can be achieved for the low-frequency characteristics generated in the low-frequency characteristic generating step and the radiation area extracted in the area extracting step on the latter stage. As a result, influences such as noise can be decreased for achieving characteristic extraction and area extraction with high accuracy, and thus calculation amounts can be decreased.

According to the radiographic image processing apparatus and program in this example of the invention, a spatial resolution is decreased twice in total. Thereby an influence such as noise is decreased and thus calculation amounts are decreased. Moreover, excessive characteristic amounts (patterns) not removed among the extracted characteristic amounts can be decreased by reduction in spatial resolution twice in total. Consequently, reduction in influence such as noise and in calculation amount can be achieved for the low-frequency characteristics and the radiation area. As a result, influences such as noise can be decreased for achieving characteristic extraction and area extraction with high accuracy, and thus calculation amounts can be decreased.

DESCRIPTION OF REFERENCES

4 . . . image processor
41 . . . low-frequency image generating section

42 . . . characteristic extracting section
43 . . . low-frequency characteristic generating section
44 . . . area extracting section
P (x, y) . . . gradient intensity
r . . . distance
θ . . . angle

DETAILED DESCRIPTION

Example 1

Figure 1:
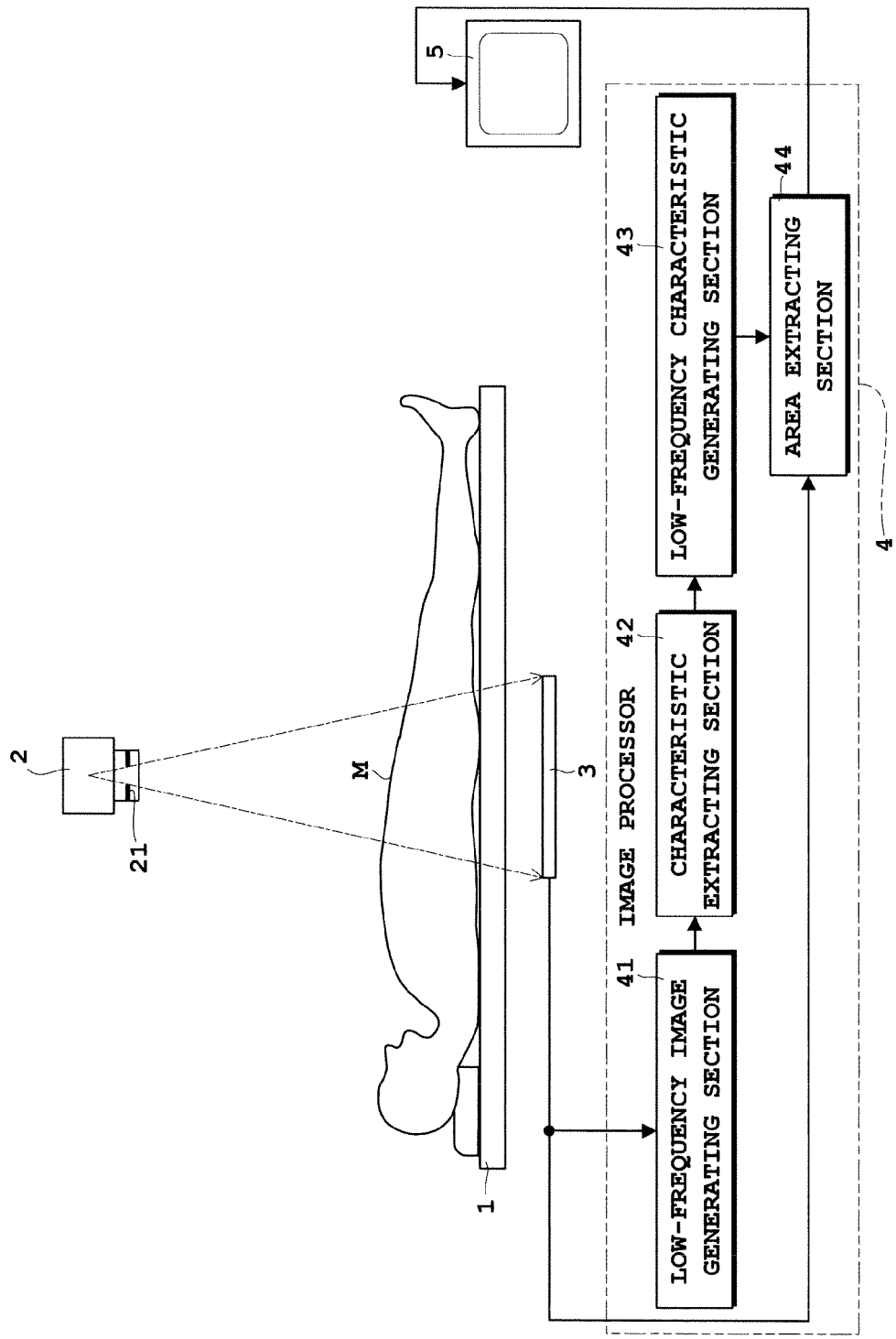
FIG. 1 is a block diagram of a radiographic image processing apparatus according to an example.
Figure 2:
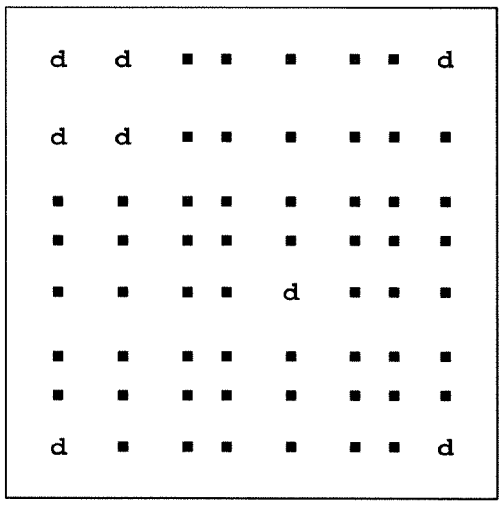
FIG. 2 is a schematic view of a detecting surface of a flat panel radiation detector (FPD).
Figure 3:
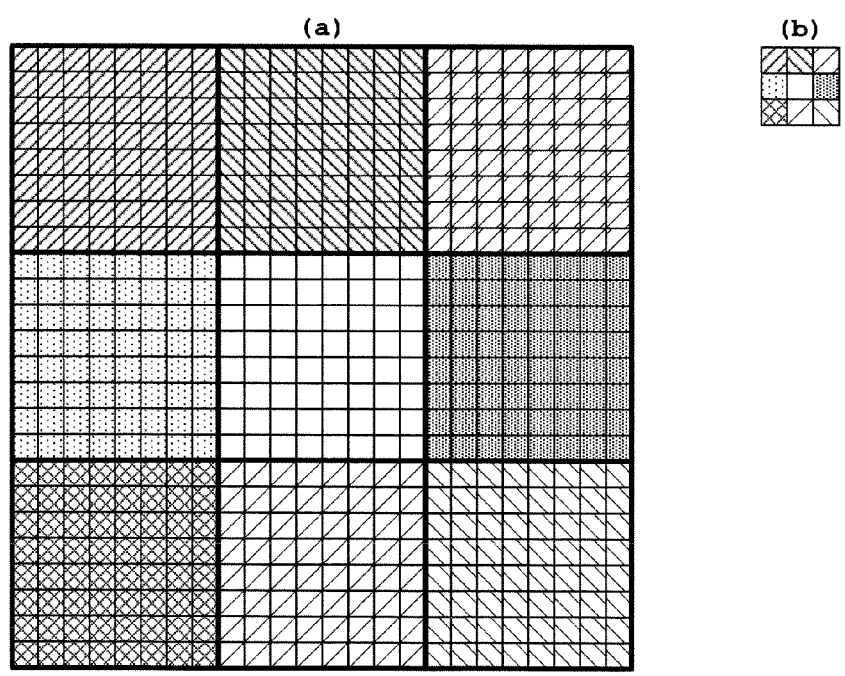
FIG. 3(a) is a schematic view of an image prior to reduction.
FIG. 3(b) is a schematic view of the image subsequent to the reduction.
Figure 4:
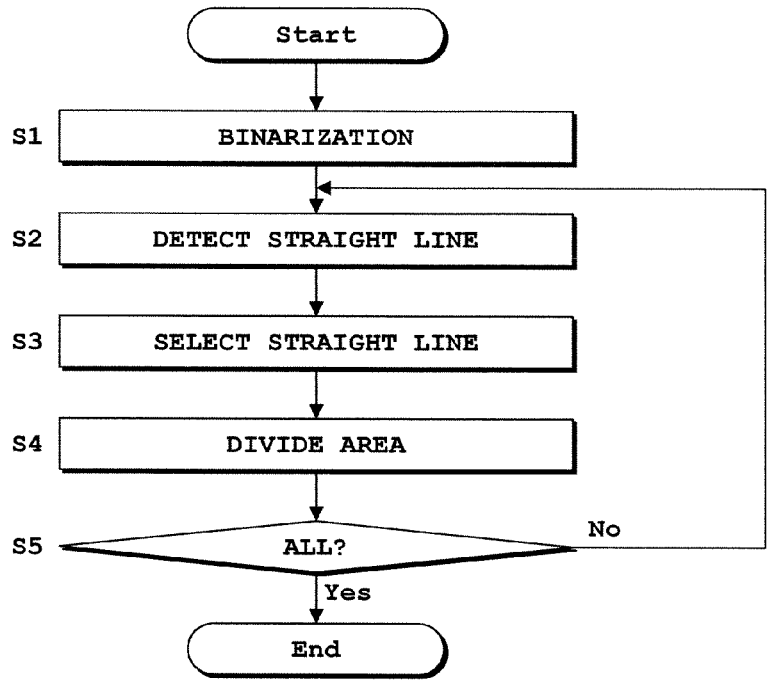
FIG. 4 is a flow chart showing a flow of a series of area extraction.
Figure 5:
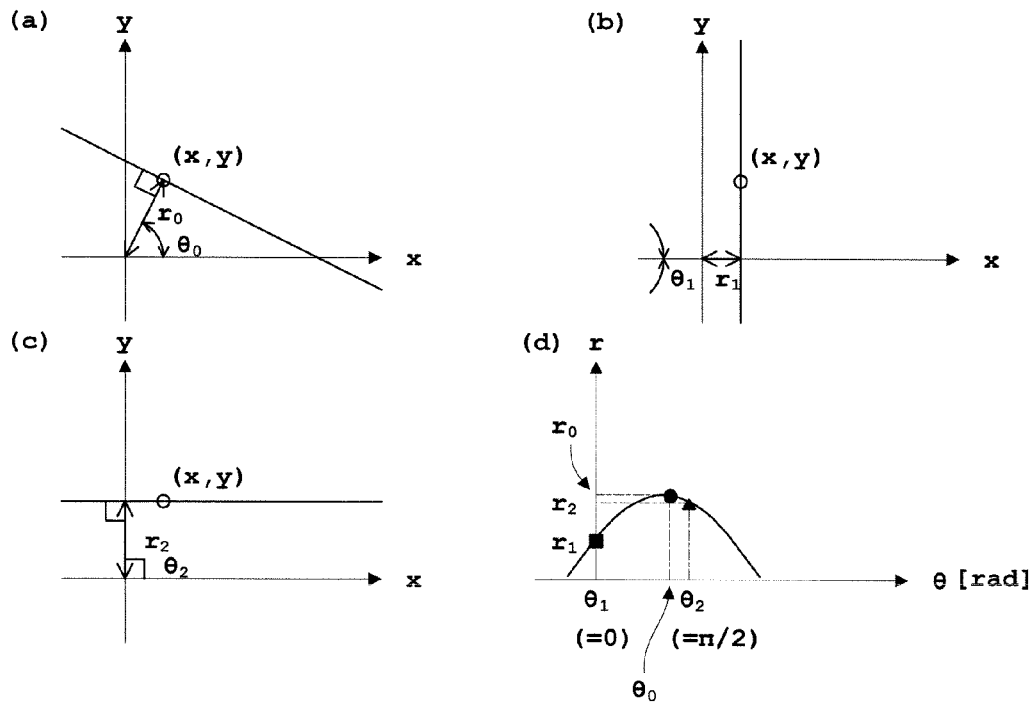
FIGS. 5(a) to 5(d) are schematic views each for explanation of a Hough transform.
Figure 6:
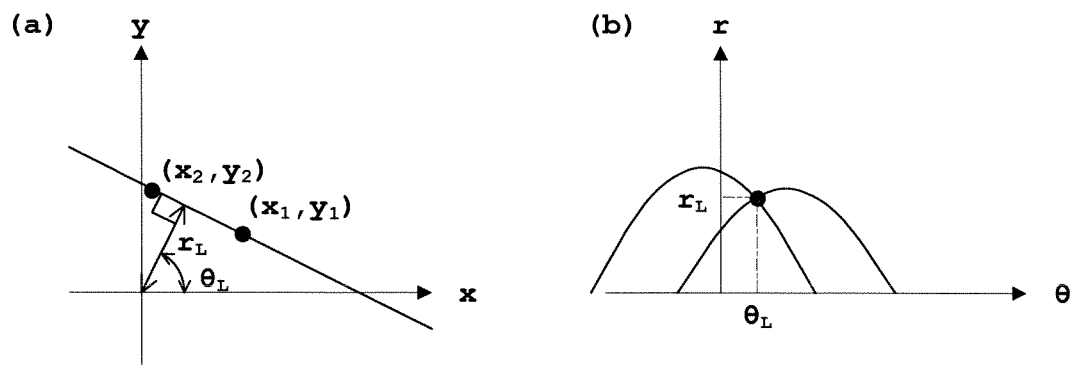
FIGS. 6(a) and 6(b) are schematic views each for explanation of a Hough transform.
Figure 7:
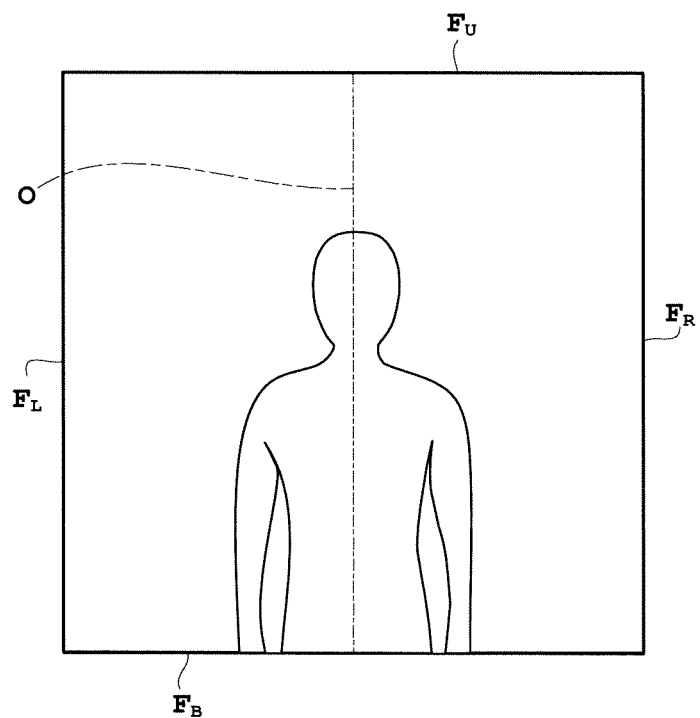
FIG. 7 is a schematic view of an image for explanation on conditions of an edge on the left-hand side of a radiation area.

One example of this invention is to be described in detail hereinafter with reference to the drawings. FIG. 1 is a block diagram of a radiographic image processing apparatus according to an example. FIG. 2 is a schematic view of a detecting surface of a flat panel radiation detector (FPD). FIG. 3(a) is a schematic view of an image prior to reduction, and FIG. 3(b) is a schematic view of the image subsequent to the reduction. FIG. 4 is a flow chart showing a flow of a series of area extraction. FIGS. 5 and 6 are schematic views each for explanation of a Hough transform. FIG. 7 is a schematic view of an image for explanation on conditions of an edge on the left-hand side of a radiation area.

As shown in FIG. 1, a radiographic image processing apparatus according to this example includes a top board 1 for supporting a subject M placed thereon, a radiation source 2 (e.g. an X-ray tube) for emitting radiation (e.g. X-rays) toward the subject M, a flat panel radiation detector (hereinafter abbreviated as "FPD") 3 for detecting radiation from the radiation source 2 through the subject M, an image processor 4 for performing image processes based on the radiation detected by the FPD 3, and a display unit 5 for displaying radiation images having undergone the image processes by the image processor 4. The display unit 5 is in the form of a display device such as a monitor, television or the like. The radiation source 2 includes a collimator 21 on an irradiation side thereof for controlling the radiation area.

The image processor 4 includes a central processing unit (CPU) and others. The programs and the like for carrying out various image processes are written and stored in a storage medium represented by a ROM (Read-only Memory). The CPU of the image processor 4 reads from the storage medium and executes the programs and the like to carry out image processes corresponding to the programs. Specifically, a low-frequency image generating section 41, a characteristic extracting section 42, a low-frequency characteristic generating section 43, and an area extracting section 44, described hereinafter, of the image processor 4 execute programs relating to generation of a low-frequency image, characteristic extraction, generation of a low-frequency characteristic, and area extraction, respectively. Thereby each of generation of a low-frequency image, characteristic extraction, generation of a low-frequency characteristic, and area extraction is performed in accordance with the program. The programs relating to generation of a low-frequency image, characteristic extraction, generation of a low-frequency characteristic, and area extraction correspond to the radiographic image processing program in this example of the invention.

The image processor 4 includes a low-frequency image generating section 41, a characteristic extracting section 42, a low-frequency characteristic generating section 43, and an area extracting section 44. The low-frequency image generating section 41 generates a low-frequency image having a lower frequency than the radiographic image through decreasing a spatial resolution of the radiographic image taken by the FPD 3. The characteristic extracting section 42 performs characteristic extraction through determining characteristic amounts in accordance with signal level differences (e.g., pixel value differences or luminance differences) between any pixel of the low-frequency image and peripheral pixels thereof to generate a characteristic image by bringing the characteristic amounts into correspondence with each pixel of the low-frequency image. The low-frequency characteristic generating section 43 generates a low-frequency characteristic as an image having a lower frequency than the characteristic image through decreasing a spatial resolution of the characteristic image. The area extracting section 44 selects a characteristic as an edge of a radiation area based on the low-frequency characteristic, and extracts the radiation area from the radiographic image. The low-frequency image generating section 41 corresponds to the low-frequency image generating device in this example of the invention. The characteristic extracting section 42 corresponds to the characteristic extracting device in this example of the invention. The low-frequency characteristic generating section 43 corresponds to the low-frequency characteristic generating device in this example of the invention. The area extracting section 44 corresponds to the area extracting device in this example of the invention.

As shown in FIG. 2, the FPD 3 has a plurality of detecting elements d sensitive to radiation on the detecting surface thereof that are arranged in a two-dimensional matrix form. The detecting elements d detect radiation by converting the radiation transmitting through the subject M into electric signals to be stored once, and reading the electric signals stored. The electric signal detected by each detecting element d is converted into a pixel value corresponding to the electric signal. The pixel value is allotted to pixels corresponding to positions of the detecting elements d, whereby a radiographic image is outputted. Then, the radiographic image is sent to the low-frequency image generating section 41 and the area extracting section 44 of the image processor 4 (see FIG. 1.)

Now, description will be given of a flow of practical radiography and data with respect to each image. An exposure button, not shown, is depressed. Thereby the radiation source 2 generates radiation to irradiate the subject M with the radiation. Radiography starts in synchronization with this. The generated radiation transmits through the subject M via the collimator 21, and enters into the FPD 3. Thereby, the FPD 3 detects radiation to output a radiographic image for radiography. As above, the collimator 21 is provided on an irradiation side of the radiation source 2. Consequently, a radiation area is determined corresponding to the shape of the collimator 21.

The radiographic image corresponding to the determined radiation area is sent to the low-frequency image generating section 41 and also to the area extracting section 44 of the image processor 4.

The low-frequency image generating section 41 generates a low-frequency image having a lower frequency than the radiographic image through decreasing a spatial resolution of the radiographic image. In this example, the low-frequency image generating section 41 generates a low-frequency image through reduction of the radiographic image. Here, any reduction ratio of the image or any size of the low-frequency image may be adopted. On the other hand, information is degraded as the reduction ratio of the image or the size of the low-frequency image is too small. Thus it is preferable that the low-frequency image is approximately one eighth the radiographic image. When the low-frequency image is generated through reduction by one eighth, a reducing process is performed through setting an average pixel value of 8×8 pixels in every direction in the radiographic image shown in FIG. 3(a) as a pixel value of one pixel in the low-frequency image shown in FIG. 3(b). Here in FIG. 3, let an area surrounded with a thick frame be 8×8 pixels in every direction. Moreover, let a part having the same hatching in FIG. 3 be 8×8 pixels in every direction prior to reduction in FIG. 3(a), and be one pixel subsequent to the reduction in FIG. 3(b), which corresponds to FIG. 3(a).

The method of generating a low-frequency image through reduction of a radiographic image (a reducing process by the low-frequency image generating section 41) is not limited to the method of determining the average value as above. It may be a reduction approach usually used such as thinning out of the pixels in the radiographic image. Moreover, the method of generating a low-frequency image is not limited to the reducing process as above. It may be an approach of generating a low-frequency image usually used. For instance, a method of generating a low-frequency image through smoothing by filtering, a method of generating a low-frequency image through converting a radiographic image into a spatial frequency area, and converting a low frequency area of the converted spatial frequency areas into a real space, or a combination of these methods may be adopted. The following method is included in examples of the method of generating a low-frequency image through converting a radiographic image into a spatial frequency area, and converting a low frequency area of the converted spatial frequency areas into a real space.

Specifically, a low-frequency image may be generated through converting a radiological image into a spatial frequency area with a Fourier transform, and removing high frequency components from the converted spatial frequency area or passing only low-frequency components, whereby a low frequency area is obtained, and then converting the low frequency area into a real space with an inverse Fourier transform. In the method using a Fourier transform and an inverse Fourier transform, a low-frequency image can be generated with no variation in size of the image. In addition, a Fourier transform is not limitative. Alternatively, a process such as a Wavelet transform or a Gabor filter may be adopted. Here, generating the low-frequency image by the low-frequency image generating section 41 corresponds to the low-frequency image generating step in this example of the invention.

The low-frequency image generated by the low-frequency image generating section 41 is sent to the characteristic extracting section 42. The characteristic extracting section 42 performs characteristic extraction through determining characteristic amounts in accordance with signal level differences (e.g., pixel value differences or luminance differences) between any pixel of the low-frequency image and peripheral pixels thereof, and generates a characteristic image by bringing the characteristic amounts into correspondence with each pixel of the low-frequency image. In this example of the invention, the characteristic image is generated through characteristic extraction by the following approach.

Specifically, a pixel value difference on light and darkness of an image (a luminance difference in the case of a monitor of the display unit 5) becomes larger adjacent to the edge of the radiation area to be finally extracted. Consequently, in this example, a pixel gradient of the image (a luminance gradient in the case of a monitor of the display unit 5) is determined as a characteristic amount. Next description will be given in detail of calculation of a gradient. Letting a pixel value in the coordinates (x, y) on the pixels be I (x, y), a characteristic amount in an x-axial direction of the characteristic amounts to be determined be Ex (x, y), a characteristic amount in a y-axial direction be Ey (x, y), the following Equations (1) and (2) are obtained.

$$Ex(x,y)=I(x+1,y)-I(x-1,y) \quad (1)$$

$$Ey(x,y)=I(x,y+1)-I(x,y-1) \quad (2)$$

Let a gradient intensity be P (x, y). Positive/negative of the characteristic amounts Ex (x, y) and Ey (x, y) is reversed and thus they may be balanced upon determination of the gradient intensity be P (x, y). Then a gradient intensity P (x, y) is calculated by taking the sum of squares as follows in Equation (3).

$$P(x,y)=\sqrt{[\{Ex(x,y)\}^2+\{Ey(x,y)\}^2]} \quad (3)$$

The method of determining a pixel gradient of the image (a luminance gradient in the case of a monitor of the display unit 5) is not limited to the method using Equation (3) mentioned above. Other well-known methods may be used.

Calculation of the characteristic amounts is not limited to calculation with the gradient using Equation (3) mentioned above. Other process may be adopted as long as an approach of extracting the signal level difference of the image as the characteristic amount. For instance, edge calculation through one dimensional or two-dimensional differentiation filtering, such as Sobel, Prewitt, Laplacian, and Canny, or extraction of high-frequency components by a frequency processing may be adopted. Moreover, another characteristics amount with a value thereof increasing at the edge of the radiation area may be used in place of the characteristic amount to be determined.

When the area extracted as a radiation area is rectangular, edges of the area exist with respect to the subject in the center of the image in the four directions corresponding to four rectangular sides. Consequently, four characteristic amounts corresponding to each edge may be determined.

Characteristic amounts are similarly determined for each pixel of the low-frequency image. Then the characteristic amounts are brought into correspondence with each pixel of the low-frequency image, whereby the characteristic image is generated. The characteristic image has the characteristic amounts of higher values at a portion with high pixel value variations (luminance variations). The characteristic extraction by the characteristic extracting section 42 corresponds to the characteristic extracting step in this example of the invention.

The characteristic amounts and the characteristic image extracted by the characteristic extracting section 42 are sent to the low-frequency characteristic generating section 43. The low-frequency characteristic generating section 43 generates a low-frequency characteristic as an image having a lower frequency than the characteristic image through decreasing a spatial resolution of the characteristic image. In this example, the low-frequency characteristic generating section 43 generates a low-frequency characteristic through reducing the characteristic image. Similar to the reducing process by the low-frequency image generating section 41, any reduction ratio of the image or any size of the low-frequency characteristic may be adopted. It is preferable that the low-frequency characteristic is approximately one eighth the characteristic image. When the low-frequency characteristic is generated by one-eighth reduction, the characteristic image shown in FIG. 3(a) is reduced into the low-frequency characteristic shown in FIG. 3(b) in the manner similar to the reduction of the radiographic image shown in FIG. 3(a) into the low-frequency image shown in FIG. 3(b). Note that the low-frequency characteristic is reduced to one sixty-fourth (=one-eighth by one-eighth) of the radiographic image.

Similar to the method of generating a low-frequency image through reduction of a radiographic image (a reducing process by the low-frequency image generating section 41), the method of generating a low-frequency characteristic through reduction of a characteristic image (a reducing process by the low-frequency characteristic generating section 43) is not limited to the method of determining the average value as above. It may be a reduction approach usually used such as thinning out of the pixels in the characteristic image. Moreover, the method of generating a low-frequency characteristic is not limited to the reducing process as above. It may be an approach of generating a low-frequency characteristic usually used. For instance, a method of generating a low-frequency characteristic through smoothing by filtering, a method of generating a low-frequency characteristic through converting a characteristic image into a spatial frequency area, and converting a low frequency area of the converted spatial frequency areas into a real space, or a combination of these methods may be adopted.

In the method of generating a low-frequency characteristic through converting a characteristic image into a spatial frequency area, and converting a low frequency area of the converted spatial frequency areas into a real space, a Fourier transform and an inverse Fourier transform may be used, which is similar to the reducing process by the low-frequency image generating section 41. In addition, a Fourier transform is not limitative. Alternatively, a process such as a Wavelet transform or a Gabor filter may be adopted. Here, generating the low-frequency characteristic by the low-frequency characteristic generating section 43 corresponds to the low-frequency characteristic generating step in this example of the invention.

The low-frequency characteristic generated by the low-frequency characteristic generating section 43 is sent to the area extracting section 44. The area extracting section 44 selects a characteristic as an edge of a radiation area based on the low-frequency characteristic, and extracts the radiation area from the radiographic image. In this example, the area extracting section 44 extracts an area by a flowchart as shown in FIG. 4.

(Step S1) Binarization

Binarization is performed to the low-frequency characteristic with the threshold set in advance, whereby binary data indicating the presence of the characteristic is prepared. For instance, where a value (gradient intensity) at any point of data in the characteristic image (coordinates on the pixel) is larger than the threshold, it is assumed that a characteristic is present and a value of "1" is assigned. Whereas a value at any point is smaller than the threshold, it is assumed that a characteristic is not present and a value of "0" is assigned. The threshold is determined in advance from empirical rules or from the average value of data of the characteristic image (gradient intensity).

The value assigned is not limited to "0" or "1." Another value or symbol may be adopted as long as the presence of the characteristic can be determined with the value. The threshold is not limited to a fixed value. It may be determined from the pixel value of the radiographic image.

(Step S2) Straight Line Detection

A pixel group is selected from the binary data that is acquired through binarization in Step S1 and indicates the presence of the characteristics for determining a linear expression. The pixel value group has pixels assumed to have characteristics that linearly continue. Thereby a linear expression is determined. Two or more straight lines may be detected.

In this example, a Hough transform is adopted as the method of determining the linear expression. A Hough transform is an approach of detecting a straight line through expressing on a two-dimensional plane (on the image) a two-dimensional straight line by a distance r of a normal line from the origin point to a straight line and an angle θ constituted by the normal line and an x-axis and projecting a characteristic point in the image (coordinates to be "1") on a Hough space for determination of the distance r and the angle θ.

First, description will be given of a Hough transform. An infinitude of straight lines passing the coordinates (x, y) on two-dimensional coordinates (here on pixels) exist, each straight line being directed in various directions. Equation (4) as follows expresses a distance r by an angle θ, and x and y.

$$r = x^* \cos \theta + y^* \sin \theta \qquad (4)$$

As is apparent from the above Equation (4), the distance r is denoted by the sine curve of the angle θ on the Hough space.

A straight line passing the coordinates (x, y) orthogonal to the distance $r_0$ from an origin point to the coordinates (x, y) is shown as in FIG. 5($a$). Here letting an angle θ constituted by the normal line and an x-axis be $\theta_0$, the straight line is projected on the Hough space at a point ($\theta_0$, $r_0$) that is drawn by a black dot in FIG. 5($d$) on the sine curve expressed by the above Equation (4).

Moreover, a straight line passing the coordinates (x, y) parallel to the y-axis is shown as in FIG. 5($b$). In this case, the distance r from the y-axis to the straight line corresponds to a distance $r_1$ from the origin point. A straight line orthogonal to the distance $r_1$ from the origin point is parallel to the y-axis. Let an angle θ at this time constituted by the normal line and the x-axis be $\theta_1$. Since the normal line is parallel to the x-axis, $\theta_1 = 0[\text{rad}]$ is given. Then $\theta_1 = 0[\text{rad}]$ is substituted for Equation (4) to yield $r_1 = x$. The straight line is projected on the Hough space at a point ($\theta_1$, $r_1$)(=(0, x)) that is drawn by a black rectangular in FIG. 5($d$) on the sine curve expressed by above Equation (4).

Moreover, a straight line passing the coordinates (x, y) parallel to the x-axis is shown as in FIG. 5($c$). In this case, the distance r from the x-axis to the straight line corresponds to a distance $r_2$ from the origin point. A straight line orthogonal to the distance $r_2$ from the origin point is parallel to the x-axis. Let an angle θ at this time constituted by the normal line and the x-axis be $\theta_2$. Since the normal line is parallel to the y-axis, $\theta_2 = \pi/2[\text{rad}]$ is given. Then $\theta_2 = \pi/2[\text{rad}]$ is substituted for Equation (4) to yield $r_2 = y$. The straight line is projected on the Hough space at a point ($\theta_2$, $r_2$) (=($\pi/2$, y)) that is drawn by a black triangle in FIG. 5($d$) on the sine curve expressed by above Equation (4).

Other than the straight line orthogonal to the distance $r_0$ from the origin point to the coordinates (x, y), the straight line parallel to the y-axis, and the straight line parallel to the x-axis, various straight lines not shown passing the coordinates (x, y) are projected on the Hough space in the same manner as above to obtain the sine curve expressed by above Equation (4) at a point (θ, r).

Next, where there are two coordinates to be noted, let one coordinates be ($x_1$, $y_1$), the other coordinates be ($x_2$, $y_2$), as shown in FIG. 6($a$). Various straight lines not shown passing the coordinates ($x_1$, $y_1$) are projected on the Hough space to obtain the sine curve as shown in FIG. 6($b$), whereas the straight lines not shown passing the coordinates ($x_2$, $y_2$) are projected on the Hough space to obtain the sine curve as shown in FIG. 6($b$).

On the other hand, let an angle constituted by the x-axis and the normal line orthogonal to the straight line passing both two coordinates ($x_1$, $y_1$) and ($x_2$, $y_2$) in FIG. 6($a$) be $\theta_L$ and let a distance r of the perpendicular from the straight line to the origin point be $r_L$. Here, the straight line in FIG. 6($a$) is orthogonal to the distance $r_L$ from the origin point. Various straight lines passing the coordinates ($x_1$, $y_1$) in FIG. 6($a$) and the coordinates $(x_2, y_2)$ in FIG. 6(a) are projected on the Hough space to obtain two sine curves as above in FIG. 6(b). The two sine curves intersect at the coordinates $(\theta_L, r_L)$. In other words, the straight line passing the two coordinates $(x_1, y_1)$ and $(x_2, y_2)$ shown in FIG. 6(a) is projected at the point $(\theta_L, r_L)$ where the two sine curves shown in FIG. 6(b) intersect.

The coordinates where the two sine curves intersect in the Hough space correspond to a straight line on the image (herein a straight line passing both two coordinates $(x_1, y_1)$ and $(x_2, y_2)$ shown in FIG. 6(a)). Here, such a Hough transform is applied to the characteristic point in the image of this example (herein the coordinates to be "1"). The coordinates of the characteristic points of the binary data obtained through binarization in Step S1 that indicates the presence of the characteristics are extracted, and various straight lines passing each coordinates are projected on the Hough space. Thereby a point $(\theta_L, r_L)$ where sine curves intersect each other and a number thereof are detected. Then the straight line with more detected (intersecting) number is extracted. The straight line orthogonal to the distance $r_L$ from the origin point at an angle $\theta_L$ constituted by the x-axis at that time is determined as a straight line to be detected. The pixel group assumed to have characteristics is to be on the straight line detected in this way.

The method of detecting a straight line from data of the characteristic image is not limited to one using a Hough transform. A least-squares method may be adopted that a straight line is determined where a square error between the straight line expressed by a linear expression and the characteristic point in the image (herein the coordinates to be "1") is minimum. Moreover, another method may be adopted as long as the method of selecting a linear characteristic. For instance, a method by matching with a template set in advance or a method of comparing correlatively with straight line data may be adopted.

Next, description will be given in detail of the method by matching with a template. For instance, an arrangement position of the collimator 21 is known in advance. Consequently, a coordinate position on the image having the collimator 21 (frame) projected thereon is set as a template. Then data where the template is consistent with the characteristic point in the image after comparison may be detected as a straight line. On the other hand, where the straight line data on the sides of the subject has been acquired as an unnecessary pattern, the straight line data on the sides of the subject is set as a template. Then data where the template is inconsistent with the characteristic point in the image after comparison may be left out as an unnecessary pattern upon detection of the straight line.

(Step S3) Straight Line Selection

Among the straight lines detected in Step S2, a straight line is selected whose position and gradient match conditions and that expresses a characteristic of highest intensity (e.g. the straight line in FIG. 6(a) having the largest number of intersection of the sine curves mentioned above). The foregoing conditions are as under when a rectangular radiation area is extracted.

<Conditions of Edge on Left Side of Radiation Area>

As shown in FIG. 7, a straight line is located on the left side relative to the center O of the subject in the image (the characteristic image in this example).

As shown in FIG. 7, an angle with the straight line and an image frame $F_L$ on the left side of the image (the characteristic image in this example) falls within a range of −45 degrees to 45 degrees. Conditions on the right side and upper and lower sides of the radiation area present the same conditions corresponding to each side (the symbol $F_R$ in FIG. 7 indicates an image frame on the right side of the image, the symbol $F_B$ an image frame on the lower side of the image, and the symbol $F_U$ an image frame on the upper side of the image.)

(Step S4) Area Division

The straight lines selected in Step S3 are each determined as an edge of the radiation area. The selected straight line has a size changed to be a size of the radiographic image, and is drawn on the radiographic image. Then the area is divided in the radiographic image corresponding to the position of the selected straight line.

(Step S5) All?

It is determined whether or not every edge (straight line) in the radiation area is detected. Where every edge is not detected, the process returns to detection of the straight line in Step S2 for performing a similar process to the other edges (straight lines). Where every edge (straight line) is detected, the area extracting section 44 completes area extraction. The area extraction (Steps S1 to S5) by the area extracting section 44 corresponds to the area extracting step in this example of the invention.

The radiation area extracted by the area extracting section 44 is sent to the display unit 5 together with the radiographic image. The display unit 5 outputs the radiation area together with the radiographic image. The radiation area may be written and stored together with the radiographic image in a storage medium represented by a RAM (Random-Access Memory) to be read out as necessary, or may be printed out by a printing device represented by a printer. The extraction results of the radiation area is outputted on the display unit 5 through displaying the line as the edge of the radiation area in the radiographic image, or through setting the pixel value other than the radiation area (a luminance value upon output on a monitor) to be "0".

According to the radiographic image processing apparatus in this example of the invention, the low-frequency image generating section 41 generates a low-frequency image having a lower frequency than a radiographic image through decreasing a spatial resolution of the radiographic image. The characteristic extracting section 42 performs characteristic extraction through determining characteristic amounts in accordance with signal level differences (in this example, pixel value differences or luminance differences) between any pixel of the low-frequency image and peripheral pixels thereof and generating a characteristic image by bringing the characteristic amounts into correspondence with each pixel of the low-frequency image. The low-frequency characteristic generating section 43 generates a low-frequency characteristic as an image having a lower frequency than the characteristic image through decreasing a spatial resolution of the characteristic image. The area extracting section 44 selects a characteristic as an edge of a radiation area based on the low-frequency characteristic, and extracts the radiation area from the radiographic image. As noted above, a spatial resolution is decreased twice in total by the low-frequency image generating section 41 and the low-frequency characteristic generating section 43. Thereby an influence such as noise and thus calculation amounts are decreased. Moreover, excessive characteristic amounts (patterns) (e.g., straight line data on sides of a subject) not removed among the characteristic amounts extracted by the low-frequency image generating section 41 and the characteristic extracting section 42 can be decreased through decrease of spatial resolution by the low-frequency characteristic generating section 43. Consequently, influence such as noise and calculation amounts can be decreased for the low-frequency characteristics generated by the low-frequency characteristic generating section 43 and the radiation area extracted by the area extracting section 44 on the latter stage. As a result, influences such as noise can be decreased for achieving characteristic extraction and area extraction with high accuracy, and thus calculation amounts can be decreased.

In this example of the invention, the low-frequency image generating section 41 generates the low-frequency image through reduction of the radiographic image as mentioned above. Reduction of the radiographic image in such manner can achieve decrease of a spatial resolution of the radiographic image to generate the low-frequency image. When the low-frequency image generating section 41 generates a low-frequency image through converting a radiographic image into a spatial frequency area, and converting a low frequency area of the converted spatial frequency area into a real space, a spatial resolution of the radiographic image is decreased through converting a low frequency area of the converted spatial frequency area into a real space to generate a low-frequency image.

In this example of the invention, the low-frequency characteristic generating section 43 generates the low-frequency characteristic through reduction of the characteristic image as mentioned above. Reduction of the characteristic image in such manner can achieve decrease of a spatial resolution of the characteristic image to generate the low-frequency characteristic. When the low-frequency characteristic generating section 43 generates a low-frequency characteristic through converting a characteristic image into a spatial frequency area, and converting a low frequency area of the converted spatial frequency areas into a real space, a spatial resolution of the characteristic image is decreased through converting a low frequency area of the converted spatial frequency area into a real space to generate a low-frequency characteristic.

In this example of the invention, the characteristic extracting section 42 extracts the characteristic as above through determining a gradient intensity $P(x, y)$ based on signal level differences (in this example, pixel value differences or luminance differences) between the pixel and the peripheral pixels.

Moreover, in this example of the invention, the area extracting section 44 preferably prepares binary data indicating the presence of a characteristic through binarization of the low-frequency characteristic from a threshold set in advance, and selects a characteristic as an edge of the radiation area based on the binary data. Preparation of the binary data as above can achieve further removal of excessive patterns (herein the coordinates to be "0".)

Moreover, in this example of the invention, using a Hough transform that converts coordinates into a space consisting of a distance r of a normal line from the origin point as a reference on a two-dimensional plane to a straight line and an angle θ constituted by the normal line and an axis (here x-axis) as a reference, the coordinates being on the two-dimensional plane, the area extracting section 44 projects the low-frequency characteristics on the space consisting of the distance r and the angle θ to determine a plurality of sine curves, and detects a straight line as a candidate of an edge of the radiation area based on a point where the sine curves intersect each other and a number thereof. The straight line is detected using such a Hough transform, whereby a straight line as a candidate of an edge of the radiation area can be detected with ease.

This invention is not limited to the foregoing embodiment, but may be modified as follows.

(1) The foregoing example of the invention has been described taking X-rays as an example of radiation. However, radiation other than X-rays (such as gamma rays) is applicable to the example.

(2) In the foregoing example of the invention, the radiographic image processing apparatus is constructed for medical use to conduct radiography of a subject placed on the top board 1 as shown in FIG. 1. This is not limitative. For example, the apparatus may be constructed like a nondestructive testing apparatus for industrial use which conducts radiography of an object (in this case, a subject tested) conveyed on a belt, or may be constructed like an X-ray CT apparatus for medical use. It may be an apparatus having a configuration that an apparatus for radiography is separated as an external apparatus and simply provided with a low-frequency image generating device, a characteristic extracting device, a low-frequency characteristic generating device, and an area-extracting device.

(3) In the foregoing example of the invention, the flat panel radiation detector (FPD) is adopted as an image sensor. The image sensor, however, is not limited to the FPD. An image sensor usually used, for example an image intensifier, can be applied to this invention. It is especially useful when a digital image sensor such as an FPD is adopted.

(4) In the foregoing example of the invention, the signal level is a pixel value or luminance. A signal level based on radiation, such as an electric signal outputted from the FPD 3, can also be adopted according to the example.

(5) In the foregoing example of the invention, the radiation area to be extracted is rectangular. This is not limited to a rectangular shape represented by a square and a rectangle. The radiation area may have a shape such as a rhombus or a parallelogram, or a shape such as a trapezoid. The radiation area of such shape can also be extracted precisely. The radiation area may also have a shape such as a polygon, an octagon, a circle, and an ellipse. The shape of the radiation area is not particularly limited as long as it is closed.

(6) Where the radiation area has a circle or ellipse shape, the edge thereof may be detected through a Hough transform for circle, a method by matching with a circular template, a method of comparing correlatively with circular data, or a least-squares method using an equation expressing a circle.

(7) In the foregoing example, the binary data is prepared through binarization of the low-frequency characteristic. The binarization is not limitative when the presence of the characteristic is classified with a threshold. For instance, two thresholds may be used. That is, where the low-frequency characteristic amount is larger than a threshold with a higher value, it is assumed that a sufficient characteristic is present and a value of "2" is assigned. Where the low-frequency characteristic amount is smaller than a threshold with a higher value and larger than a threshold with a lower value, it is assumed that a little characteristic is present and a value of "1" is assigned. Moreover, where the low-frequency characteristic amount is smaller than the threshold with a lower value, it is assumed that a characteristic is not present and a value of "0" is assigned. Thereby ternary data is prepared. In this way, data may be prepared through division into three or more values. When a straight line is detected using an intersection of sine curves, ternary data, for example, may be used. That is, where the characteristic is sufficient (where the value is larger than the threshold with a higher value), weighting of "2", for example, is performed. Where the characteristic is a little (where the value is smaller than the threshold with a higher value and larger than the threshold with a lower value), weighting of "1", for example, is performed. Thereby a straight line can be detected preciously. Alternatively, a straight line may be detected through setting a value proportional to the value of the characteristic amount for a space. In this case, the binarization in Step S1 shown in FIG. 4 is not needed.

The invention claimed is:

1. A radiographic image processing apparatus for processing a radiographic image having undergone radiography, comprising:
a low-frequency image generating device for generating a low-frequency image having a lower frequency than the radiographic image through decreasing a spatial resolution of the radiographic image;
a characteristic extracting device for performing characteristic extraction through determining characteristic amounts in accordance with signal level differences between any pixel of the low-frequency image and peripheral pixels thereof and generating a characteristic image by bringing the characteristic amounts into correspondence with each pixel of the low-frequency image;
a low-frequency characteristic generating device for generating a low-frequency characteristic as an image having a lower frequency than the characteristic image through decreasing a spatial resolution of the characteristic image; and
an area extracting device for selecting a characteristic as an edge of a radiation area based on the low-frequency characteristic, and extracting the radiation area from the radiographic image.

2. The radiographic image processing apparatus according to claim 1, wherein
the low-frequency image generating device generates the low-frequency image through reducing the radiographic image.

3. The radiographic image processing apparatus according to claim 1, wherein
the low-frequency image generating device generates the low-frequency image through converting the radiographic image into a spatial frequency area, and then converting a low frequency area of the converted spatial frequency area into a real space.

4. The radiographic image processing apparatus according to claim 1, wherein
the low-frequency image generating device generates the low-frequency image through smoothing by filtering to the radiographic image.

5. The radiographic image processing apparatus according to claim 1, wherein
the low-frequency characteristic generating device generates the low-frequency characteristic through reduction of the characteristic image.

6. The radiographic image processing apparatus according to claim 1, wherein
the low-frequency characteristic generating device generates the low-frequency characteristic through converting the characteristic image into a spatial frequency area, and then converting a low frequency area of the converted spatial frequency area into a real space.

7. The radiographic image processing apparatus according to claim 1, wherein
the low-frequency characteristic generating device generates the low-frequency characteristic through smoothing by filtering to the characteristic image.

8. The radiographic image processing apparatus according to claim 1, wherein
the area extracting device extracts the characteristic through determining a gradient intensity based on signal level differences between the pixel and the peripheral pixels.

9. The radiographic image processing apparatus according to claim 1, wherein
the area extracting device prepares binary data indicating the presence of a characteristic through binarization of the low-frequency characteristic from a threshold set in advance, and selects a characteristic as an edge of the radiation area based on the binary data.

10. The radiographic image processing apparatus according to claim 1, wherein
using a Hough transform that converts coordinates into a space consisting of a distance of a normal line from the origin point as a reference on a two-dimensional plane to a straight line and an angle constituted by the normal line and an axis as a reference, the coordinates being on the two-dimensional plane,
the area extracting device projects the low-frequency characteristics on the space consisting of the distance and the angle to determine a plurality of sine curves, and detects a straight line as a candidate of an edge of the radiation area based on a point where sine curves intersect each other and a number thereof.

11. A radiographic image processing program for processing a radiographic image by a computer, comprising
a low-frequency image generating step generating a low-frequency image having a lower frequency than the radiographic image through decreasing a spatial resolution of the radiographic image;
a characteristic extracting step performing characteristic extraction through determining characteristic amounts in accordance with signal level differences between any pixel of the low-frequency image and peripheral pixels thereof and generating a characteristic image by bringing the characteristic amounts into correspondence with each pixel of the low-frequency image;
a low-frequency characteristic generating step generating a low-frequency characteristic as an image having a lower frequency than the characteristic image through decreasing a spatial resolution of the characteristic image; and
an area extracting step selecting a characteristic as an edge of a radiation area based on the low-frequency characteristic, and extracting the radiation area from the radiographic image,
the computer executing processes in the steps.

* * * * *